(12) United States Patent
Durst et al.

(10) Patent No.: US 7,279,499 B2
(45) Date of Patent: Oct. 9, 2007

(54) SUBSTITUTED BENZOPYRANS AS SELECTIVE ESTROGEN RECEPTOR-BETA AGONISTS

(75) Inventors: Gregory Lee Durst, Indianapolis, IN (US); Bryan Hurst Norman, Indianapolis, IN (US); Lance Allen Pfeifer, Indianapolis, IN (US); Timothy Ivo Richardson, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 273 days.

(21) Appl. No.: 10/549,106

(22) PCT Filed: Apr. 8, 2004

(86) PCT No.: PCT/US2004/009271

§ 371 (c)(1), (2), (4) Date: Sep. 14, 2005

(87) PCT Pub. No.: WO2004/094401

PCT Pub. Date: Nov. 4, 2004

(65) Prior Publication Data

US 2006/0199858 A1    Sep. 7, 2006

(51) Int. Cl.
*C07D 311/76* (2006.01)
*C07D 311/94* (2006.01)

(52) U.S. Cl. .................. 514/454; 549/385; 549/390

(58) Field of Classification Search ............... 514/454; 549/385, 390
See application file for complete search history.

(56) References Cited

U.S. PATENT DOCUMENTS 6,630,508 B1   10/2003   Dodge et al.

FOREIGN PATENT DOCUMENTS

| GB | 2 361 642 | 10/2001 |
| WO | WO 97/09348 | 9/1996 |
| WO | WO 99/02512 | 1/1999 |
| WO | WO 01/49673 | 7/2001 |
| WO | WO 01/64665 | 9/2001 |
| WO | WO 01/72713 | 10/2001 |
| WO | WO 03/044006 | 5/2003 |
| WO | WO 03/051805 | 6/2003 |

OTHER PUBLICATIONS

Anderson, et al., "Synthesis of 6,9-bisnormethyl-8-methoxy-12,13-epoxy-6,8,10-trichothec atriene," Journal of Organic Chemistry, American Chemisal Society, Easton, U.S., vol. 42, No. 6, pp. 1045-1050 (1977).
Oude-Alink, et al., "Photolysis of 2-keto-2,3-dihydrobenzofurans, o-hydroxystyrenes and 1-o-hydroxyphenyl)-1,5-hexadienes," Journal of Organic Chemistry, American Chemical Society, Easton, U.S., vol. 38, No. 11, pp. 1993-2001 (1973).
Shrestha, et al., "Facile synthesis of the fused 6-6-5 ring system containing chroman ring from 2-(1-hydroxy-5-alkenyl)phenol derivatives via intramolecular inverse-electron-demanddiels-alder reaction," Bulletin of the Chemical Society of Japan, Japan Publications Trading Co., Tokyl, JP, vol. 72, No. 1, pp. 73-83 (1999).
Welhua, et al., "A role for estrogen receptor β in the regulation of growth of the ventral prostate," PNAS, vol. 98, No. 11, pp. 6330-6335 (2001).
Mortensen, et al., "Synthesis and biological evaluation of a novel series of furans: ligands selectic for estrogen receptor α," Journal of Medicinal Chemistry, A-K, Page Est. 10:8 (2001).
Meyers, "Estrogen receptor-β potency-selective ligands: structure-activity relationship studies of diarylpropionitriles and their acetylene and polar analogues," Journal of Medicinal Chemistry, A-V, Page Est. 21:3 (2001).

*Primary Examiner*—Bernard Dentz
(74) *Attorney, Agent, or Firm*—John C. Demeter

(57) ABSTRACT

The present invention relates to substituted benzopyran derivatives, stereoisomers, and pharmaceutical acceptable salts thereof and processes for the preparation of the same. The compounds of the present invention are useful as Estrogen Receptor ? agonists. Such agonists are useful for the treating Estrogen Receptor ? mediated diseases such as prostate cancer or BPH.

12 Claims, No Drawings

SUBSTITUTED BENZOPYRANS AS SELECTIVE ESTROGEN RECEPTOR-BETA AGONISTS

BACKGROUND OF THE INVENTION

The present invention relates to novel cycloalkyl-benzopyrans and derivatives thereof, compositions containing those compounds, their use as selective estrogen receptor-beta agonists, and their use in the treatment of estrogen receptor-beta mediated diseases such as prostate cancer, benign prostatic hyperplasia (hypertrophy), testicular cancer, ovarian cancer, lung cancer, cardiovascular diseases, neurodegenerative disorders, urinary incontinence, central nervous system (CNS) disorders, gastrointestinal (GI) tract disorders, and osteoporosis.

Estrogens play important roles in the development and homeostasis of the reproductive, central nervous, skeletal, and cardiovascular systems of both males and females. Recently, a new ER isoform, ER-beta (also known as ER-beta1) was cloned from a rat prostatic cDNA library and is present in murine and human prostates. Consequently, the previous ER is now designated as ER-alpha. ER-alpha and ER-beta share high amino acid homology, have similar 17-β Estradiol (E2) binding affinities, and can hetero- or homodimerize to form a signaling complex; Kuiper G G, et al., Endocrinol. 138: 863-70 (1997); Kuiper G G et al., Proc. Natl. Acad. Sci. USA 93: 5925-30 (1996). Although E2 activates both ER-alpha and ER-beta, ER-alpha stimulates transcription and cellular proliferation, while ER-beta suppresses ER-alpha activation. Interestingly, 3-Beta, 17-beta-androstanediol and 5-alpha-androstane have been proposed to be endogenous ligands for ER-beta; Weihua Z. et al. PNAS 98:6330-5 (2001). 3-Beta, 17-beta-androstanediol is a major metabolite of dihydrotestosterone (DHT), the 5-alpha-reduced active intracellular androgen in male accessory sex organs. ER-beta activation also stimulates increased glutathione S-transferase and quinone reductase expression. These two enzymes have been shown to possess chemoprotective detoxification properties; Chang W Y et al., Prostate 40: 115-24 (1999); Montano M M et al., J. Biol. Chem. 273: 25443-9 (1998).

With the recent identification of ER-beta, and the recognition that ER-alpha and ER-beta have different biological roles, ER-selective modulators would similarly possess significant clinical utility. Since ER-beta is strongly expressed in a number of tissues including prostate, bladder, ovary, testis, lung, small intestine, vascular endothelium, and various parts of the brain, compounds that selectively modulate ER-beta would be of clinical importance in the treatment of a variety of disease conditions, such as prostate cancer, testicular cancer, ovarian cancer, lung cancer, cardiovascular diseases, neurodegenerative disorders, urinary incontinence, CNS disorders, GI tract disorders, and osteoporosis. Such compounds would have minimal effect on tissues that contain ER-alpha, and thus exhibit different side-effect profiles. Thus, ER-beta agonists will display different therapeutic profiles compared to ER-alpha antagonists or agonists, and would be preferentially beneficial in tissues relying on ER-beta signaling.

The prostate gland produces components that are found in the semen and blood. Some of these are regulatory peptides. The prostate gland comprises stroma and epithelium cells, the latter group consisting of columnar secretory cells and basal non-secretory cells. The proliferation of these basal cells, as well as stroma cells gives rise to benign prostatic hyperplasia (BPH), which is one common prostate disease. BPH is a progressive condition that is characterized by the nodular enlargement of the prostatic tissue resulting in obstruction of the urethra. This results in increased frequency of urination, noncuria, poor urine stream, and hesitation or delay in starting the urine flow. Consequences of BPH can include hypertrophy of bladder smooth muscle, decompensated bladder, and increased incidence of urinary tract infection. The development of BPH is considered to be an inescapable phenomenon for the aging male population. BPH is observed in approximately 70% of males over the age of 70. Drug treatment for BPH currently employs alpha andrenergic antagonists for symptomatic relief or steroid 5-alpha reductase inhibitors to reduce hyperplastic tissue bulk. These approaches are of limited therapeutic benefit.

BRIEF SUMMARY OF THE INVENTION

The present invention relates to novel benzopyran derivatives of formula (I):

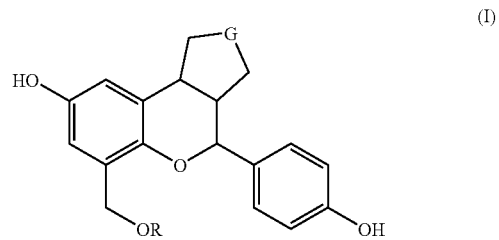

wherein R is hydrogen or $C_1$-$C_6$ alkyl; and
G is —$CH_2$— or —$CH_2CH_2$—;
including the enantiomers thereof.

Compounds of the invention include the following, which should not be construed as in any way limiting the compounds included in the invention:

a) (3aR, 4S, 9bS)-4-(4-Hydroxy-phenyl)-6-methoxymethyl-1,2,3,3a,4,9b-hexahydro-cyclopenta[c]chromen-8-ol;

b) (3aS, 4R, 9bR)-4-(4-Hydroxy-phenyl)-6-methoxymethyl-1,2,3,3a,4,9b-hexahydro-cyclopenta[c]chromen-8-ol;

c) (3aR, 4S, 9bS)-6-Hydroxymethyl-4-(4-hydroxy-phenyl)-1,2,3,3a,4,9b-hexahydro-cyclopenta[c]chromen-8-ol;

d) (3aS, 4R, 9bR)-6-Hydroxymethyl-4-(4-hydroxy-phenyl)-1,2,3,3a,4,9b-hexahydro-cyclopenta[c]chromen-8-ol;

e) (3aR, 4S, 9bS)-6-Ethoxymethyl-4-(4-hydroxy-phenyl)-1,2,3,3a,4,9b-hexahydro-cyclopenta[c]chromen-8-ol;

f) (3aS, 4R, 9bR)-6-Ethoxymethyl-4-(4-hydroxy-phenyl)-1,2,3,3a,4,9b-hexahydro-cyclopenta[c]chromen-8-ol;

and the enantiomers thereof.

In a second embodiment, the present invention provides a pharmaceutical composition comprising a therapeutically effective amount of a compound of formula (I) and a pharmaceutically acceptable carrier.

In a further embodiment, the present invention provides medical methods of employing compounds formula (I) as agonists of estrogen receptor ("ER") beta, further utilized for the treatment of ER beta-mediated diseases such as prostate cancer, benign prostatic hyperplasia, testicular cancer, cardiovascular diseases, neurodegenerative disorders, urinary incontinence, central nervous system (CNS) disorders, gastrointestinal (GI) tract disorders, and osteoporosis.

DETAILED DESCRIPTION OF THE INVENTION

As used in this application:

a) the term "halo" refers to a fluorine atom, chlorine atom, bromine atom, or iodine atom;

b) the term "$C_1$-$C_6$ alkyl" refers to a branched or straight chained alkyl radical containing from 1 to 6 carbon atoms, such as methyl (Me), ethyl (Et), n-propyl, isopropyl, n-butyl, isobutyl, sec butyl, t-butyl (t-Bu), pentyl, hexyl, etc.;

c) the designation " ~~ " refers to a bond for which the stereochemistry is not designated;

d) the designation " ▬ " refers to a bond that protrudes forward out of the plane of the page;

e) the designation " ⦙⦙⦙ " refers to a bond that protrudes backward out of the plane of the page;

f) as used in the preparations and examples the following terms have the indicated meanings; "ng" refers to nanograms; "µg" refers to micrograms; "mg" refers to milligrams; "g" refers to grams; "kg" refers to kilograms; "nmole" refers to nanomoles; "mmol" refers to millimoles; "mol" refers to moles; "µL" refers to microliters; "mL" refers to milliliters; "L" refers to liters; "$R_f$" refers to retention factor; "° C." refers to degrees Celsius; "bp" refers to boiling point; "mm of Hg" refers to pressure in millimeters of mercury; "mp" refers to melting point; "dec" refers to decomposition; "$[\alpha]^{20}_D$" refer to specific rotation of the D line of sodium at 20° C. obtained in a 1 decimeter cell; "c" refers to concentration in g/mL; "nM" refers to nanomolar; "µM" refers to micromolar; "mM" refers to millimolar; "M" refers to molar; "$K_i$" refers to inhibiton constant; "$K_d$" refers to dissociation constant; "psi" refers to pounds per square inch; "rpm" refers to revolutions per minute; "HPLC" refers to high performance liquid chromatography; "HRMS" refers to high resolution mass spectrum; "THF" refers to tetrahydrofuran; "brine" refers to a saturated aqueous solution of sodium chloride; "L.O.D." refers to loss on drying; "µCi" refers to microcuries; "i.p." refers to intraperitoneally; "i.v." refers to intravenously; and "DPM" refers to disintegrations per minute;

g) the term "enantiomeric excess" or "ee" refers to the percent by which one enantiomer, E1, is in excess in a mixture of the two enantiomers, E1 plus E2, such that {(E1-E2)÷(E1+E2)}×100=ee.

The compounds used in the method of the present invention may have one or more asymmetric centers. As a consequence of these chiral centers, the compounds of the present invention occur as racemates and as individual enantiomers, as well as diastereomers and mixtures of diastereomers. All asymmetric forms, individual isomers and combinations thereof, are within the scope of the present invention.

In order to preferentially prepare one optical isomer over its enantiomer, a number of routes are available. As an example, a mixture of enantiomers may be prepared, and then the two enantiomers may be separated. A commonly employed method for the separation of a racemic mixture is the use of chiral high pressure liquid chromatography. Further details regarding resolution of enantiomeric mixtures may be found in J. Jacques, et al., Enantiomers, Racemates, and Resolutions, (1991). "The term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (I). Illustrative inorganic acids that form suitable salts include hydrochloric, hydrobromic, sulphuric, and phosphoric acid and acid metal salts such as sodium monohydrogen orthophosphate, and potassium hydrogen sulfate. Illustrative organic acids that form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxy-benzoic, p-toluenesulfonic acid, and sulfonic acids such as benzenesulfonic acid, methanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (I). Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Illustrative examples of the compounds encompassed by the present invention include the racemic mixtures and specific enantiomers of the following compounds:

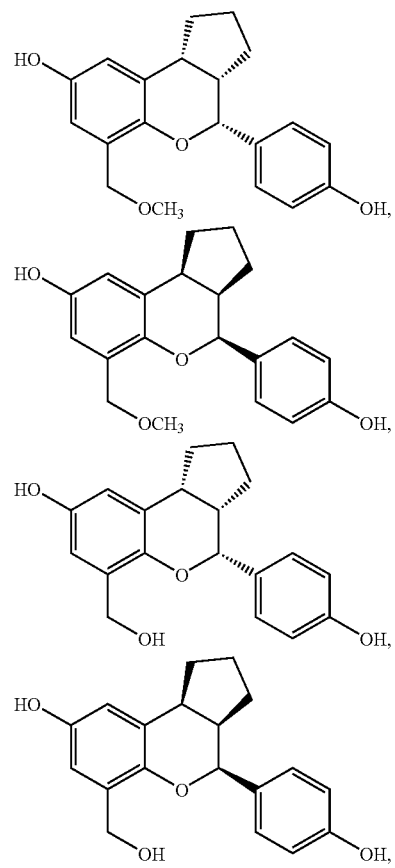

-continued

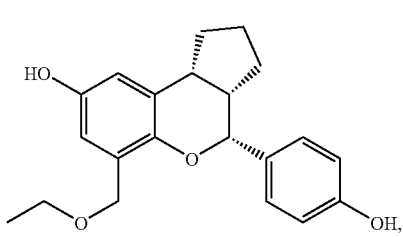

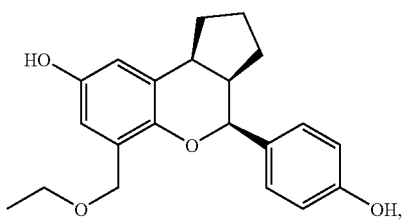

Reaction Schemes

Compounds of formula (I) and intermediates thereof can be prepared as described in Reaction Schemes A-E. All substituents, unless otherwise indicated, are previously defined. The reagents and starting materials are readily available to one of ordinary skill in the art.

SCHEME A

-continued

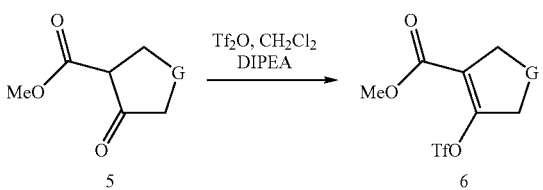

4-Methoxy phenol is treated with a suitable brominating agent, such as benzyltrimethylammonium tribromide, in a suitable solvent, such as methanol (MeOH) and methylene chloride ($CH_2Cl_2$) to provide the dibromide 2. Demethylation with a suitable demethylating agent, such as trimethylsilyl iodide (TMSI), in a suitable polar solvent such as acetonitrile ($CH_3CN$), gives the hydroquinone 3 which is then protected as the bis-methoxymethyl (MOM) ether 4 using a suitable strong base, such as a metal hydride, most preferably sodium hydride (NaH), in a suitable solvent, such as dimethylforamide (DMF). To this suspension is added an amount of an alkoxymethyl ether chloride, preferably chloromethyl methyl ether (MOMCl), which corresponds to a roughly equimolar amount depending on the number of hydroxy groups to be protected on the phenol of formula 3.

SCHEME B

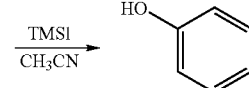

$G = -CH_2-; -CH_2CH_2-$

Treatment of β-ketoester 5 with an appropriate amount of a triflating agent, such as trifluoromethanesulfonic(triflic) anhydride ($Tf_2O$) in the presence of a suitable base, such as diisopropylethylamine (DIPEA), and an appropriate aprotic solvent, such as methylene chloride ($CH_2Cl_2$), gives the enol triflate 6. 4-Bromophenol is protected with a suitable protecting group, such as methoxymethyl ether (MOM), to give the protected derivative 8 using a suitable strong base, such as a metal hydride, most suitably sodium hydride, in a suitable anhydrous solvent, such as anhydrous dimethylformamide (DMF). To this suspension is added an appropriate amount of an alkoxymethyl ether chloride, preferably chloromethyl methyl ether (MOMCl), generally in the molar ratio equivalent to each hydroxy group to be protected.

SCHEME C

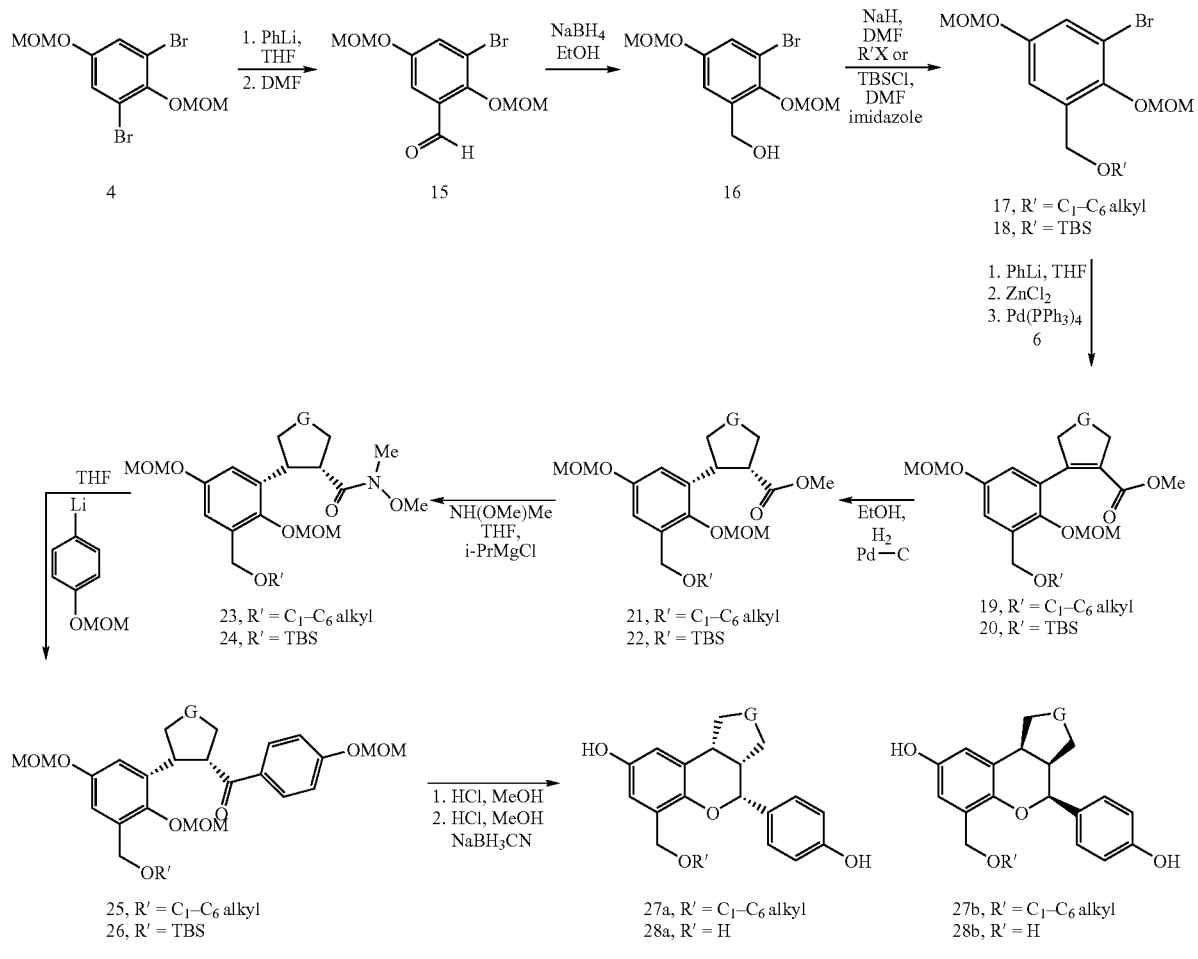

R' = H, C$_1$-C$_6$ alkyl
G = —CH$_2$—; —CH$_2$CH$_2$—

Ortho mono-lithiation of the protected hydroquinone 4 from scheme A with a suitable lithiation agent, such as phenyllithium, in a suitable anhydrous solvent, such as THF, is followed by quenching of the anion with a suitable formylating agent, such as N,N-dimethylformamide (DMF), to provide the carbonyl substituted derivative 15. Reduction of the aldehyde 15 with a suitable reducing agent, such as sodium borohydride, in a suitable solvent, such as ethanol, provides the benzyl alcohol 16. Benzyl alcohol 16 may then be converted to a C$_1$-C$_6$ alkyl ether derivative 17 by treatment with a suitable strong base, such as an anhydrous metal hydride, most preferably sodium hydride, and the addition of a suitable C$_1$-C$_6$ alkyl halide. Benzyl alcohol 16 may alternatively be converted to the silyl ether derivative 18 by treatment with a suitable base, such as imidazole, and the addition of tert-butyldimethylsilyl chloride. A second ortho lithiation of ethers 17 and 18 is followed by coupling with enol triflate 6 from scheme B using Negeshi conditions, as described above in scheme C, (Negeshi, E. Acc. Chem. Res. 1982, 15, 340-348) to give the unsaturated esters 19 and 20. Unsaturated esters 19 and 20 are then hydrogenated over palladium on carbon (Pd—C) under hydrogen in an appropriate solvent, such as EtOH, to give 21 and 22, which are then transformed into racemic Weinreb amides 23 and 24, using an appropriate Grignard reagent, such as isopropyl-magnesium chloride (iPr—MgCl), and N,O-dimethylhydroxylamine-HCl (HN(Ome)Me) in an appropriate solvent, such as THF, as would be known to one skilled in the art and as also described above in scheme C. Racemic Weinreb amides 23 and 24 are reacted with lithiated p-bromophenyl methoxymethyl ether in an appropriate solvent, such as THF, to give the racemic ketones 25 and 26. Deprotection and cyclization of ketones 25 and 26 under acidic conditions, such as in the presence of an appropriate acid, such as HCl in MeOH, is followed by reduction with a selective reducing agent, such as sodium cyanoborohydride (NaBH$_3$CN), under acidic conditions, such as HCl in methanol, to give racemic benzopyrans 27 and 28. The racemic benzopyrans are then separated into their individual enantiomers (27a and 27b; 28a and 28b) using chiral preparative HPLC, using methods well known to one skilled in the art.

SCHEME D

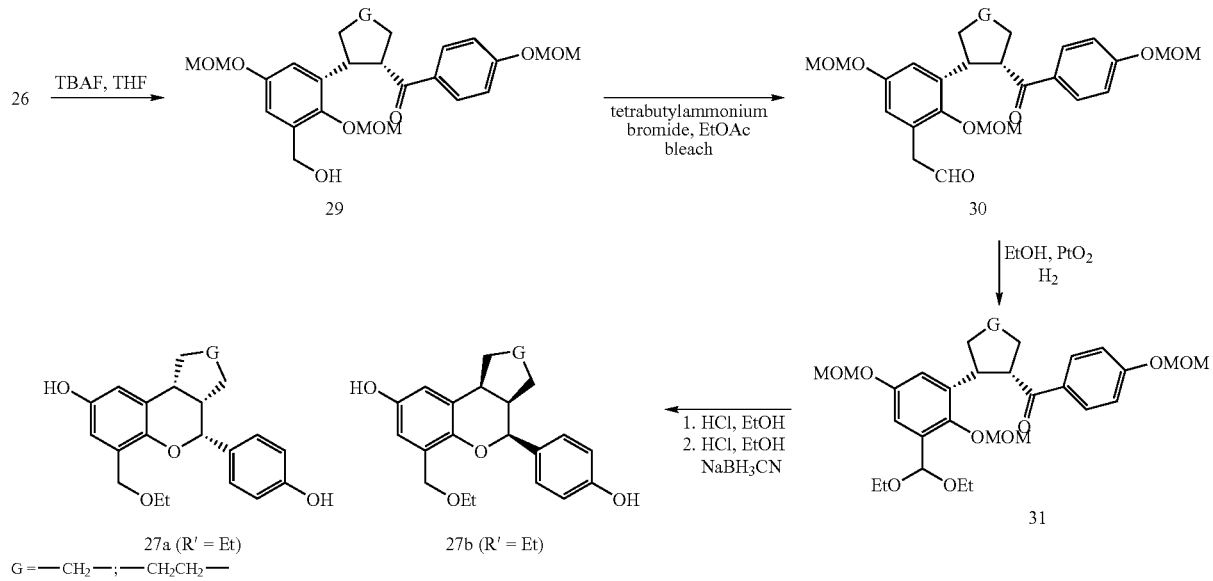

G = —CH₂—; —CH₂CH₂—

Deprotection of the tert-butyldimethylsilyl protected benzyl ether 26 from scheme D with a suitable fluoride source, such as tetrabutylammonium fluoride (TBAF), in a suitable solvent, such as THF, gives the benzyl alcohol 29, which is oxidized with bleach in ethyl acetate (EtOAc) under phase transfer conditions (such as tetra-butyl ammonium bromide) to give the racemic benzaldehyde 30. Reduction of benzaldehyde 30 using hydrogenation conditions, under a hydrogen atmosphere in the presence of a suitable catalyst, such as, platinum oxide (PtO₂), in an appropriate solvent, such as EtOH, produces the racemic diethyl acetal derivative 31. Deprotection and cyclization of 31 under acidic conditions, such as HCl in ethanol, as would be known to one skilled in the art, is followed by reduction with a suitable reducing agent, such sodium cyanoborohydride (NaBH₃CN) under acidic conditions, such as HCl in ethanol, to give racemic benzopyran 27 directly. The racemic benzopyran is then separated into its individual enantiomers (27a and 27b) using chiral preparative HPLC, as would be known by one skilled in the art.

Preparation 1

Preparation of
1,3-dibromo-2,5-bis-methoxymethoxy-benzene

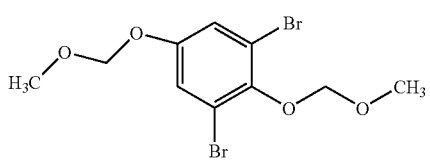

A. Preparation of 2,6-dibromo-4-methoxy-phenol

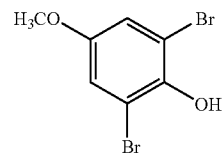

To 4-methoxyphenol (10.00 g, 80.6 mmol) in CH₂Cl₂ (70 mL), add a stirred solution of benzyltrimethylammonium tribromide (69.10 g, 177.2 mmol) in CH₂Cl₂ (500 mL) and MeOH (200 mL). Stir the reaction for 12 hours and remove the solvent in vacuo. Add methyl tert-butyl ether (MTBE) (600 mL) and collect the precipitate (benzyltrimethylammonium bromide) by filtration and wash with MTBE (200 mL). Filter the organics through Celite® and concentrate to provide the subtitled product (23.0 g, >95%) as an orange solid that may be used without purification. ¹H NMR (DMSO-d₆) δ 3.69 (s, 3H), 7.14 (s, 2H), 9.32 (s, 1H).

B. Preparation of 2,6-dibromo-benzene-1,4-diol

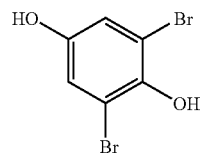

Dissolve 2,6-dibromo-4-methoxyphenol (23.0 g, 80.6 mmol) in CH₃CN (400 mL) and add trimethylsilyl iodide (TMSI) (53 mL, 371 mmol). Reflux the solution for 4 hours and add more TMSI (50 mL, 371 mmol). Heat the reaction at reflux overnight and cool to ambient temperature. Pour into ice-H₂O (700 mL) and extract with EtOAc (2×300 mL). Wash the combined extracts with saturated sodium hydrosulfite (200 mL), H₂O (200 mL) and brine (100 mL), dry over MgSO₄, filter and concentrate. Crystallize the residue to provide the subtitled product (21.36 g, 98%) as a tan crystalline solid.

$^1$H NMR (DMSO-d$_6$) δ 6.94 (s, 2H), 9.07 (s, 1H), 9.56 (s, 1H).

C. Preparation of 1,3-dibromo-2,5-bis-methoxymethoxy-benzene

Add sodium hydride (7.11 g of 95% dry, 0.282 mol) in portions to a 1 L three-necked flask equipped with nitrogen inlet, magnetic stir bar and DMF (300 mL) at −10 to −15° C. Add a solution of 2,6-dibromo-benzene-1,4-diol (34.25 g, 0.128 mol) in DMF (100 mL) over about 20 min, maintaining the internal temperature of the reaction below −5° C. Stir the reaction for 1 hour and then add methoxymethyl chloride (MOMCl) (19.93 mL, 0.262 mol) in portions. Maintain the internal temperature below −5° C. Stir the mixture for 3 hours and add ice until gas evolution ceases. Pour the reaction into ice-H₂O (600 mL) and extract with EtOAc (2×500 mL). Combine the organic extracts, wash with 1 N NaOH (500 mL) and brine (400 mL). Dry the solution (MgSO₄), filter and concentrate to provide the title compound (43.4 g, 95%) as an oil which may be used without further purification. $^1$H NMR (CDCl₃) δ 3.46 (s, 3H), 3.71 (s, 3H), 5.10 (s, 4H), 7.23 (s, 2H).

Preparation 2

Preparation of 2-trifluoromethanesulfonyloxy-cyclopent-1-enecarboxylic acid methyl ester

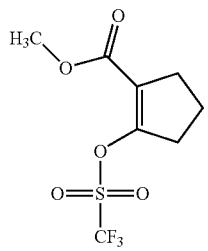

Slowly add a solution of methyl 2-oxocyclopentanecarboxylate (21.0 g, 148 mmol) in CH₂Cl₂ (30 mL) to a −78° C. solution of N,N,-diisopropylethylamine (DIPEA) (129 mL, 738 mmol) in CH₂Cl₂ (670 mL). Keep the reaction temperature below −65° C. Then slowly add a solution of trifluoromethanesulfonic anhydride (50.0 g, 177 mmol) in CH₂Cl₂ (30 mL) to the reaction, keeping the reaction temperature below −65° C. After 1.5 hours, quench the reaction with H₂O (500 mL) and warm to room temperature. Separate the layers and extract the aqueous layer with CH₂Cl₂ (2×100 mL). Combine the organic extracts, dry (Na₂SO₄), filter and concentrate. Pre-absorb the crude material onto silica gel. Purify using silica gel chromatography, eluting with Hex:EtOAc (90:10) to provide the title product (34.3 g, 85%) as a light yellow oil. $^1$H NMR (CDCl₃) δ 1.97-2.07 (m, 2H), 2.68-2.78 (m, 4H), 3.79 (s, 3H). CIMS (Methane) m/z 275 [C₈H₉F₃O₅S+H]$^+$.

Preparation 3

Preparation of 1-Bromo-4-methoxymethoxy-benzene

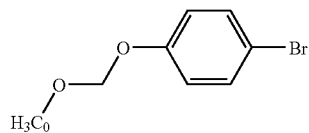

Add sodium hydride (2.78 g of 95% dry, 0.116 mol) in portions to a 500 mL three-necked flask equipped with a nitrogen inlet, magnetic stir bar and DMF (200 mL) at −10 to −15° C. Add a solution of 4-bromophenol (20.00 g, 0.116 mol) in DMF (100 mL) over about 20 minutes, maintaining the internal temperature of the reaction below −5° C. Stir the reaction for 1 hour and then add MOMCl (8.81 mL, 0.116 mol) in portions to maintain the internal temperature below −5° C. Stir the mixture for 3 hours and then add ice until gas evolution ceases. Pour the reaction into ice-H₂O (500 mL) and extract with EtOAc (2×300 mL). Wash the combined organic extracts with 1 N NaOH (500 mL), H₂O (500 mL) and brine (400 mL). Dry the solution (MgSO₄), filter and concentrate to obtain the title product (23.94 g, 93%) as an oil which may be used without further purification. $^1$H NMR (CDCl₃) δ 3.46 (s, 3H), 5.14 (s, 2H), 6.92 (d, J=9.0 Hz, 2H), 7.37 (d, J=9.0 Hz, 2H).

Preparation 4

Preparation of (3-bromo-2,5-bis-methoxymethoxy-phenyl)-methanol

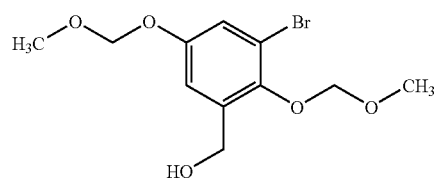

A. Preparation of 3-bromo-2,5-bis-methoxymethoxy benzaldehyde

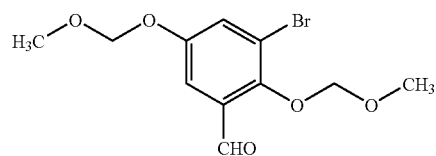

Add a solution of phenyllithium (7.80 mL of a 1.8 M solution in cyclohexane-Et₂O (70:30), 14.04 mmol) over 15 seconds to a −78° C. solution of 1,3-dibromo-2,5-bis-methoxymethoxy-benzene (5.00 g, 14.04 mmol) in THF (100 mL). After stirring the reaction for 15 minutes, add DMF (2.17 mL, 28.08 mmol) and stir the reaction for 1 hour. Pour the reaction into H$_2$O (150 mL) and extract with EtOAc (2×100 mL). Combine the organic extracts, wash with brine, dry (MgSO$_4$), filter and concentrate. Purify the crude material using silica gel chromatography, eluting with Hex:EtOAc (80:20) to afford the subtitled product (3.00 g, 70%) as an oil. $^1$H NMR (CDCl$_3$) δ 3.47 (s, 3H), 3.61 (s, 3H), 5.14 (s, 2H), 5.16 (s, 2H), 7.45 (d, J=3.0 Hz, 1H), 7.53 (d, J=3.1 Hz, 1H), 10.29 (s, 1H).

B. Preparation of (3-bromo-2,5-bis-methoxymethoxy-phenyl)-methanol

Treat a solution of 3-bromo-2,5-bis-methoxymethoxy benzaldehyde (9.40 g, 30.6 mmol) in EtOH (200 mL) with sodium borohydride (1.16 g, 30.6 mmol). Stir the reaction for 2 hours at ambient temperature and pour into H$_2$O (200 mL) and saturated NaHCO$_3$ (100 mL). Extract the H$_2$O with EtOAc (3×100 mL) and wash the combined extracts with H$_2$O (100 mL) and brine (50 mL) then dry (MgSO$_4$) and filter. Concentrate the filtrate to afford the title product (9.31 g, 99%) as an oil. $^1$H NMR (CDCl$_3$) δ 3.20 (t, J=6.9 Hz, 1H), 3.47 (s, 3H), 3.64 (s, 3H), 4.60 (d, J=6.9 Hz, 2H), 5.08 (s, 2H), 5.13 (s, 2H), 7.02 (d, J=2.9 Hz, 1H), 7.23 (d, J=2.9 Hz, 1H).

EXAMPLES

In the following examples, the following chromatography methods as herein described and as referred to in the examples may be used.
1. TLC data was recorded on silica gel.
2. $^1$H NMR data was recorded at 300 MHz using tetramethyl silane as the internal standard.
3. Melting points are uncorrected.
4. HPLC methods are outlined below.

Method A: Waters Symmetry C18, 60A column (4.6×250 mm). The elution system consisted of a gradient of 95:5 (0.1% TFA in H2O)/(0.1% TFA in CH$_3$CN) isocratic elution for 5 min followed by gradient elution from 95:5 to 0:100 (0.1% TFA in H$_2$O)/(0.1% TFA in CH$_3$CN) over 15 min, followed by (0.1% TFA in CH$_3$CN) isocratic elution for 5 min. The flow rate was 1 mL/min. UV detection was performed at 220 nm.

Method B: Chiralpak AD column (50×500 mm). Isocratic elution with 85:15 (Heptane/EtOH). The flow rate was 118 ml/min. UV detection was performed at 220 nm.

Method C: Chiralpak AD column (4.6×250 mm) column. Isocratic elution with 85:15 (Heptane/EtOH). The flow rate was 1 mL/min. UV detection was performed at 220 nm.

Method D: Chiralpak AD column (4.6×250 mm) column. Isocratic elution with 90:10 (Heptane/EtOH). The flow rate was 1 mL/min. UV detection was performed at 220 nm.

Method E: Chiralpak AD column (50×500 mm). Isocratic elution with 80:20 (Heptane/EtOH). The flow rate was 118 mL/min. UV detection was performed at 220 nm.

Method F: Chiralpak AD column (4.6×250 mm) column. Isocratic elution with 80:20 (Heptane/IPA). The flow rate was 1 mL/min. UV detection was performed at 220 nm.

Method G: Chiralpak AD column (4.6×250 mm) column. Isocratic elution with 40:60 (Heptane/EtOH). The flow rate was 1 mL/min. UV detection was performed at 220 nm.

Method H: Chiralpak AD column (50×500 mm) column. Isocratic elution with 40:60 (Heptane/EtOH). The flow rate was 118 mL/min. UV detection was performed at 220 nm.

Examples 1A and 1B

Preparation of (3aR, 4S, 9bS)-4-(4-Hydroxy-phenyl)-6-methoxymethyl-1,2,3,3a,4,9b-hexahydro-cyclopenta[c]chromen-8-ol and (3aS, 4R, 9bR)-4-(4-Hydroxy-phenyl)-6-methoxymethyl-1,2,3,3a,4,9b-hexahydro-cyclopenta[c]chromen-8-ol

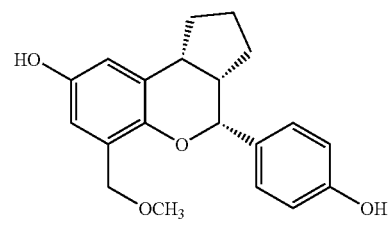

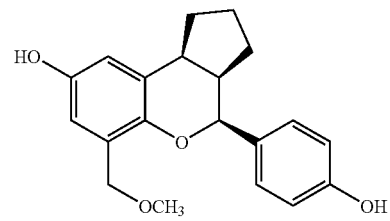

A. Preparation of 1-bromo-2,5-bis-methoxymethoxy-3-methoxymethyl-benzene

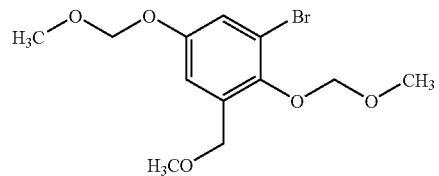

Add sodium hydride (0.430 g of 60% in oil, 10.75 mmol) to DMF (100 mL) at −5° C. Add (3-bromo-2,5-bis-methoxymethoxy-phenyl)-methanol (3.00 g, 9.77 mmol) in DMF (20 mL) in portions and stir the resulting solution at −5° C. for 1 hour. Add methyl iodide (0.67 mL, 10.75 mmol) and stir the reaction for 1 hour. Pour the reaction into ice-H$_2$O (200 mL) and extract with EtOAc (2×50 mL). Combine the extracts and wash with H$_2$O (2×100 mL) and brine (50 mL) then dry (MgSO$_4$), filter and concentrate. Purify the residue by silica gel chromatography eluting with Hex:EtOAc (80:20) to provide the subtitled product (2.76 g, 88%) as an oil. $^1$H NMR (CDCl$_3$) δ 3.41 (s, 3H), 3.47 (s, 3H), 3.62 (s, 3H), 4.54 (s, 2H), 5.03 (s, 2H), 5.13 (s, 2H), 7.06 (d, J=2.9 Hz, 1H), 7.20 (d, J=2.9 Hz, 1H).

B. Preparation of 2-(2,5-Bis-methoxymethoxy-3-methoxymethyl-phenyl)-cyclopent-1-enecarboxylic acid methyl ester

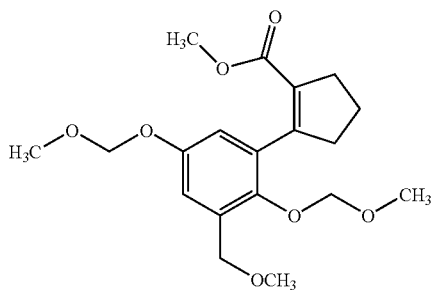

Purge a solution of 1-bromo-2,5-bis-methoxymethoxy-3-methoxymethyl-benzene (2.76 g, 8.59 mmol) in THF (17 mL) with nitrogen and cool to −70° C. Clowly add a solution of phenyllithium (4.3 mL of a 2.0 M solution in dibutyl ether, 8.59 mmol) to the cooled solution, keeping the temperature below −60° C. After 35 minutes, add a solution of $ZnCl_2$ (8.6 mL of a 1.0 M solution in $Et_2O$, 8.59 mmol) and warm the reaction to 0° C. Purge a solution of 2-trifluoromethanesulfonyloxy-cyclopent-1-enecarboxylic acid methyl ester (2.36 g, 8.59 mmol) in THF (17 mL) with nitrogen. To the cooled zincate solution, add $Pd(PPh_3)_4$ (0.496 g, 0.430 mmol) followed by the triflate solution. Heat this mixture to 50° C. overnight then cool to room temperature. Quench the reaction with $H_2O$ and extract with EtOAc (3×50 mL). Combine the organic extracts, dry ($Na_2SO_4$), filter and concentrate. Purify the crude material using silica gel chromatography eluting with Hex:EtOAc (75:25, then 50:50) to afford the subtitled product (1.76 g, 56%) as an oil. $^1$H NMR ($CDCl_3$) δ 1.95-2.05 (m, 2H), 2.78-2.85 (m, 4H), 3.42 (s, 3H), 3.47 (s, 6H), 3.57 (s, 3H), 4.51 (s, 2H), 4.80 (s, 2H), 5.12 (s, 2H), 6.74 (d, J=3.1 Hz, 1H), 7.04 (d, J=3.1 Hz, 1H).

C. Preparation of (±)-2-(2,5-Bis-methoxymethoxy-3-methoxymethyl-phenyl)-cyclopentanecarboxylic acid methyl ester

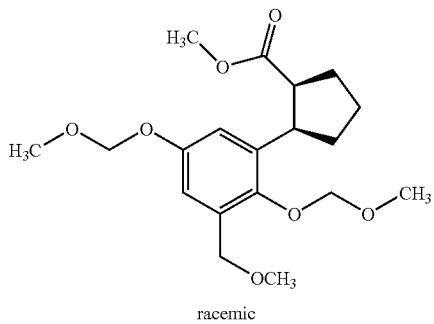

racemic

Stir a solution of 2-(2,5-bis-methoxymethoxy-3-methoxymethyl-phenyl)-cyclopent-1-enecarboxylic acid methyl ester (1.76 g, 4.80 mmol) in EtOH (75 mL, pre-filtered through a plug of basic alumina) for 1 minute with activated carbon, then filter through Celite®. Add 10% Pd/C (50% wet, 0.83 g) to the filtrate and hydrogenate this mixture at 55-60 psi for at least 20 hours. Filter the reaction through Celite® and concentrate the filtrate to afford the subtitled product (1.20 g, 68%) as an oil that may be used without further purification. $^1$H NMR ($CDCl_3$) δ 1.63-1.74 (m, 1H), 1.92-2.10 (m, 4H), 2.11-2.20 (m, 1H), 3.20-3.27 (m, 4H), 3.40 (s, 3H), 3.46 (s, 3H), 3.60 (s, 3H), 3.69-3.78 (m, 1H), 4.44-1.53 (m, 2H), 4.95-5.01 (m, 2H), 5.08-5.14 (m, 2H), 6.80 (d, J=3.0 Hz, 1H), 6.94 (d, J=3.0 Hz, 1H).

D. Preparation of (±)-2-(2,5-Bis-methoxymethoxy-3-methoxymethyl-phenyl)-cyclopentanecarboxylic acid methoxy-methyl-amide

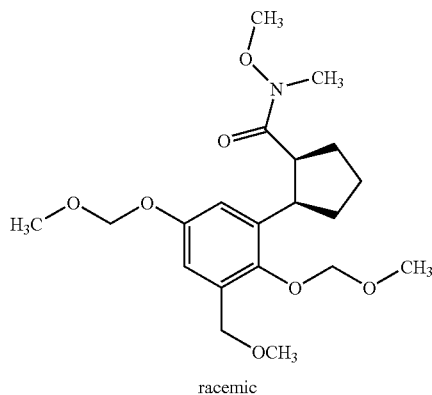

racemic

Use conditions analogous to those described in Step D of Examples 1A and 1B to react (±)-2-(2,5-bis-methoxymethoxy-3-methoxymethyl-phenyl)-cyclopentanecarboxylic acid methyl ester (1.20 g, 3.26 mmol) and N,O-dimethylhydroxylamine hydrochloride (0.476 g, 4.88 mmol) to afford the subtitled product (1.25 g, 97%) as an oil that may be used without further purification. $^1$H NMR ($CDCl_3$) δ 1.67-1.72 (m, 1H), 1.87-1.95 (m, 2H), 2.02-2.08 (m, 2H), 2.10-2.19 (m, 1H), 2.86 (s, 3H), 3.33 (br s, 3H), 3.38 (s, 3H), 3.45 (s, 3H), 3.50-3.59 (m, 1H), 3.60 (s, 3H), 3.68-3.74 (m, 1H), 4.45 (s, 2H), 4.91-4.96 (m, 2H), 5.07-5.13 (m, 2H), 6.89-6.92 (m, 2H).

E. Preparation of (±)-[2-(2,5-Bis-methoxymethoxy-3-methoxymethyl-phenyl)-cyclopentyl]-4-methoxymethoxy-phenyl)-methanone

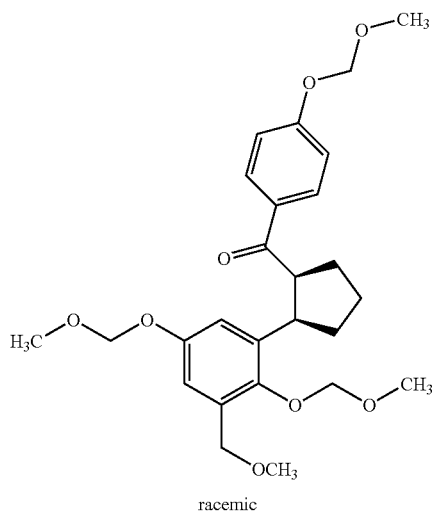

racemic

Use conditions analogous to those described in Step E of Examples 1A and 1B to couple (±)-2-(2,5-bis-methoxymethoxy-3-methoxymethyl-phenyl)-cyclopentanecarboxylic acid methoxy-methyl-amide (1.25 g, 3.14 mmol) and 1-bromo-4-methoxymethoxy-benzene (1.36 g, 6.29 mmol) to afford the subtitled product (1.21 g, 81%) as an oil. $^1$H NMR (CDCl$_3$) δ 1.70-1.81 (m, 1H), 1.90-2.16 (m, 4H), 2.23-2.33 (m, 1H), 3.23 (s, 3H), 3.38 (s, 3H), 3.43 (s, 3H), 3.60 (s, 3H), 3.82-3.90 (m, 1H), 4.17 (d, J=11.9 Hz, 1H), 4.20-4.28 (m, 1H), 4.33 (d, J=11.9 Hz, 1H), 4.90 (s, 2H), 4.93 (d, J=6.6 Hz, 1H), 5.00 (d, J=6.6 Hz, 1H), 5.12 (s, 2H), 6.66 (s, 2H), 6.80 (d, J=-8.8 Hz, 2H), 7.62 (d, J=8.8Hz, 2H).

F. Preparation of (3aR, 4S, 9bS)-4-(4-Hydroxyphenyl)-6-methoxymethyl-1,2,3,3a,4,9b-hexahydro-cyclopenta[c]chromen-8-ol and (3aS, 4R, 9bR)-4-(4-Hydroxy-phenyl)-6-methoxymethyl-1,2,3,3a,4,9b-hexahydro-cyclopenta[c]chromen-8-ol Use conditions analogous to those described in Examples 1A and 1B to cyclize [2-(2,5-bis-methoxymethoxy-3-methoxymethyl-phenyl)-cyclopentyl]-(4-methoxymethoxy-phenyl)-methanone (1.21 g, 2.55 mmol) to provide racemic material (0.775 g, 93%). Separate the racemic mixture with a Chiralpak AD column (Method E) to afford Example 3A (0.300 g, 36%). Further purify the (−)-enantiomer using silica gel chromatography, eluting with Hex:EtOAc (75:25, then 50:50) to afford Example 3B (0.162 g, 19%).

Example 1A

R$_f$ 0.14 (75:25 Hex/EtOAc).; mp 91-95° C.; [α]$^{25}_D$+31.9° (c 0.28, MeOH).; $^1$H NMR (DMSO-d$_6$) δ 1.23-1.41 (m, 4H), 1.61-1.65 (m, 1H), 1.99-2.08 (m, 1H), 2.54-2.60 (m, 1H), 3.28 (s, 3H), 3.36-3.40 (m, 1H), 4.37 (s, 2H), 4.91 (s, 1H), 6.47 (d, J=2.6 Hz, 1H), 6.55 (d, J=2.6 Hz, 1H), 6.75 (d, J=8.5 Hz, 2H), 7.22 (d, J=8.5 Hz, 2H), 8.80 (s, 1H), 9.30 (s, 1H).; FAB MS m/z 326 [C$_{20}$H$_{22}$O$_4$]$^+$.; HPLC (Method A) 98.7% (area percent), t$_R$=17.9 min.; % ee (Method F)>99%, t$_R$=8.2 min.; Anal. Calcd for C$_{20}$H$_{22}$O$_4$·0.25H$_2$O: C, 72.60; H, 6.85.; Found: C, 72.52; H, 6.76.

Example 1B

R$_f$ 0.14 (75:25 Hex/EtOAc).; mp 76-80° C.; [α]$^{25}_D$−33.1° (c 0.25, MeOH).; $^1$H NMR (DMSO-d$_6$) δ 1.23-1.41 (m, 4H), 1.61-1.65 (m, 1H), 1.99-2.08 (m, 1H), 2.54-2.60 (m, 1H), 3.28 (s, 3H), 3.36-3.40 (m, 1H), 4.37 (s, 2H), 4.91 (s, 1H), 6.47 (d, J=2.6 Hz, 1H), 6.55 (d, J=2.6 Hz, 1H), 6.75 (d, J=8.5 Hz, 2H), 7.22 (d, J=8.5 Hz, 2H), 8.80 (s, 1H), 9.30 (s, 1H).; FAB MS m/z 326 [C$_{20}$H$_{22}$O$_4$]$^+$.; HPLC (Method A)>99% (area percent).; t$_R$=18.0 min.; % ee (Method F)>98%, t$_R$=12.8 min.; Anal. Calcd for C$_{20}$H$_{22}$O$_4$·0.6H$_2$O: C, 71.24; H, 6.93.; Found: C, 71.37; H, 6.59.

Examples 2A and 2B

Preparation of (3aR, 4S, 9bS)-6-Hydroxymethyl-4-(4-hydroxy-phenyl)-1,2,3,3a,4,9b-hexahydro-cyclopenta[c]chromen-8-ol and (3aS, 4R, 9bR)-6-Hydroxymethyl-4-(4-hydroxy-phenyl)-1,2,3,3a,4,9b-hexahydro-cyclopenta[c]chromen-8-ol

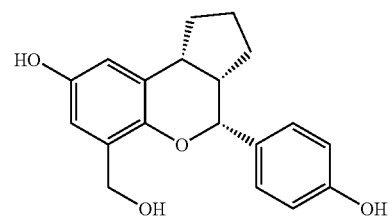

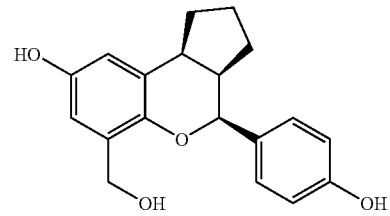

A. Preparation of (3-Bromo-2,5-bis-methoxymethoxy-benzyloxy)-tert-butyl-dimethyl-silane

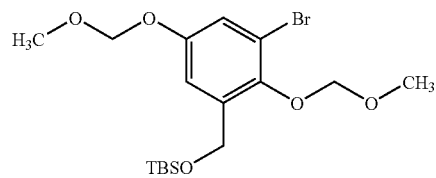

Prepare a solution of (3-bromo-2,5-bis-methoxymethoxy-phenyl)-methanol (1.46 g, 4.76 mmol) and imidazole (0.357 g, 5.24 mmol) in DMF (50 mL). Add tertbutyldimethylsilyl chloride (TBSCl) (0.790 g, 5.24 mmol). Stir the reaction for 3 hours and pour into cold H$_2$O (150 mL). Extract the H$_2$O with EtOAc (3×50 mL), combine the extracts, and wash with H$_2$O (2×50 mL) and brine (20 mL). Dry (MgSO$_4$), filter and concentrate to afford the subtitled product (1.95 g, >95%) as an oil that may be used without purification. $^1$NMR (CDCl$_3$) δ 0.11 (s, 6H), 0.95 (s, 9H), 3.47 (s, 3H), 3.51 (s, 3H), 4.84 (s, 2H), 5.02 (s, 2H), 5.12 (s, 2H), 7.15 (d, J=2.9 Hz, 1H), 7.17 (d, J=3.0 Hz, 1H).

B. Preparation of 2-[3-(tert-Butyl-dimethyl-silanyloxymethyl)-2,5-bis-methoxymethoxy-phenyl]-cyclopent-1-enecarboxylic acid methyl ester

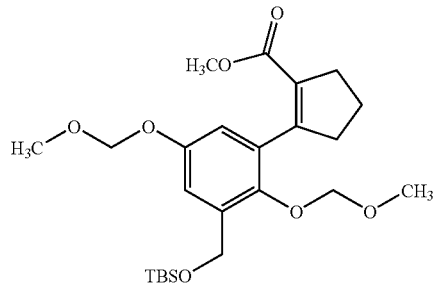

Use conditions analogous to those described in Step B of Examples 1A and 1B to react (3-bromo-2,5-bis-methoxymethoxy-benzyloxy)-tert-butyl-dimethyl-silane (1.90 g, 4.51 mmol) with phenyllithium (2.96 mL of a 1.8 M solution in cyclohexane-Et$_2$O (70:30), 4.51 mmol), ZnCl$_2$ (5.32 mL of a 1 M solution in Et$_2$O, 4.51 mmol), 2-trifluoromethanesulfonyloxy-cyclopent-1-enecarboxylic acid methyl ester (1.46 g, 4.51 mmol) and Pd(PPh$_3$)$_4$ (0.61 g, 0.532 mmol). Purify the material by silica gel chromatography eluting with Hex:EtOAc (95:5) to afford the subtitled product (0.77 g, 36%) as an oil. $^1$H NMR (CDCl$_3$) δ 0.12 (s, 6H), 0.96 (s, 9H), 1.96-2.04 (m, 2H), 2.77-2.83 (m, 4H), 3.46 (s, 3H), 3.47 (s, 3H), 3.56 (s, 3H), 4.78 (s, 2H), 4.81 (s, 2H), 5.12 (s, 2H), 6.69 (d, J=3.1 Hz, 1H), 7.15 (d, J=3.1 Hz, 1H).

C. Preparation of (±)-2-[3-(tert-Butyl-dimethyl-silanyloxymethyl)-2,5-bis-methoxymethoxy-phenyl]-cyclopentanecarboxylic acid methyl ester

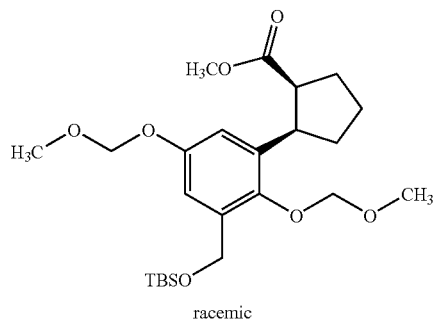

racemic

Filter a solution of 2-[3-(tert-butyl-dimethyl-silanyloxymethyl)-2,5-bis-methoxymethoxy-phenyl]-cyclopent-1-enecarboxylic acid methyl ester (0.715 g, 1.53 mmol) in EtOH (40 mL) through a 1×6 cm pad of activated carbon. Add the filtrate to a Parr® bottle containing 10% Pd/C (50% wet, 0.15 g) and hydrogenate this mixture at 55-60 psi for 3 hours. Filter the reaction through Celite® and concentrate the filtrate to afford the subtitled product (0.605 g, 84%) as an oil that may be used without further purification. $^1$H NMR (CDCl$_3$) δ 0.10 (s, 3H), 0.11 (s, 3H), 0.94 (s, 9H), 1.60-1.67 (m, 1H), 1.91-2.04 (m, 4H), 2.11-2.18 (m, 1H), 3.22 (s, 3H), 3.17-3.24 (m, 1H), 3.45 (s, 3H), 3.58 (s, 3H), 3.65-3.72 (m, 1H), 4.79 (s, 2H), 4.95 (dd, J=5.8, 6.8 Hz, 2H), 5.10 (dd, J=6.6, 9.6 Hz, 2H), 6.74 (d, J=3.0 Hz, 1H), 7.04 (d, J=3.0 Hz, 1H).

D. Preparation of (±)-2-[3-(tert-Butyl-dimethyl-silanyloxymethyl)-2,5-bis-methoxymethoxy-phenyl]-cyclopentanecarboxylic acid methoxy-methyl-amide

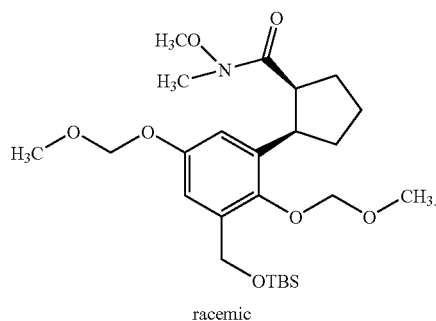

racemic

Use conditions analogous to those described in Step D of Examples 1A and 1B to react (±)-2-[3-(tert-butyl-dimethyl-silanyloxymethyl)-2,5-bis-methoxymethoxy-phenyl]-cyclopentanecarboxylic acid methyl ester (0.605 g, 1.29 mmol) and N,O-dimethylhydroxylamine hydrochloride (0.189 g, 1.94 mmol) in the presence of isopropylmagnesium chloride (2.13 mL, 4.26 mmol) to afford the subtitled product (0.622 g, 97%) as an oil that may be used without further purification.

$^1$H NMR (CDCl$_3$) δ 0.09 (s, 3H), 0.10 (s, 3H), 0.93 (s, 9H), 1.62-1.73 (m, 1H), 1.86-1.94 (m, 2H), 2.04-2.10 (m, 2H), 2.17-2.28 (m, 1H), 2.85 (s, 3H), 3.13 (s, 3H), 3.45 (s, 3H), 3.58 (s, 3H), 3.48-3.59 (m, 1H), 3.60-3.69 (m, 1H), 4.76 (s, 2H), 4.89-4.96 (m, 2H), 5.06-5.12 (m, 2H), 6.85 (d, J=3.0 Hz, 1H), 7.02 (d, J=3.0 Hz, 1H).

E. Preparation of (±)-{2-[3-(tert-Butyl-dimethyl-silanyloxymethyl)-2,5-bis-methoxymethoxy-phenyl]-cyclopentyl}-(4-methoxymethoxy-phenyl)-methanone

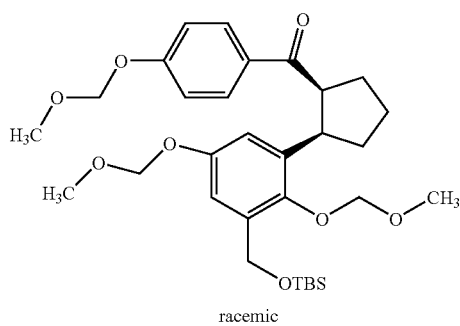

racemic

Use conditions analogous to those described in Step E of Examples 1A and 1B to couple (±)-2-[3-(tert-butyl-dimethyl-silanyloxymethyl)-2,5-bis-methoxymethoxy-phenyl]-cyclopentanecarboxylic acid methoxy-methyl-amide (0.622 g, 1.25 mmol) and 1-bromo-4-methoxymethoxy-benzene (0.543 g, 2.50 mmol). Purify the material by silica gel chromatography eluting with Hex:EtOAc (90:10) to afford the subtitled product (0.549 g, 76%) as an oil. $^1$H NMR (CDCl$_3$) δ 0.02 (s, 3H), 0.04 (s, 3H), 0.90 (s, 9H), 1.72-1.77 (m, 1H), 1.91-2.12 (m, 4H), 2.21-2.30 (m, 1H), 3.38 (s, 3H), 3.43 (s, 3H), 3.59 (s, 3H), 3.80-3.87 (m, 1H), 4.18-4.25 (m, 1H), 4.55 (dd, J=13.6, 44.7 Hz, 2H), 4.89 (dd, J=5.9, 7.5 Hz, 2H), 4.95 (dd, J=6.6, 20.3 Hz, 2H), 5.12 (dd, J=6.8, 7.9 Hz, 2H), 6.61 (d, J=3.0 Hz, 1H), 6.75 (d, J=3.0 Hz, 1H), 6.81 (d, J=8.9 Hz, 2H), 7.63 (d, J=8.9 Hz, 2H).

F. Preparation of (3aR, 4S, 9bS)-6-Hydroxymethyl-4-(4-hydroxy-phenyl)-1,2,3,3a,4,9b-hexahydro-cyclopenta[c]chromen-8-ol and (3aS, 4R, 9bR)-6-Hydroxymethyl-4-(4-hydroxy-phenyl)-1,2,3,3a,4,9b-hexahydro-cyclopenta[c]chromen-8-ol Use conditions analogous to those described in Examples 1A and 1B to cyclize (±)-{2-[3-(tert-butyl-dimethyl-silanyloxymethyl)-2,5-bis-methoxymethoxy-phenyl]-cyclopentyl}-(4-methoxymethoxy-phenyl)-methanone (0.549 g, 1.11 mmol) to provide racemic material (0.285 g, 82%). Separate the racemic mixture with a Chiralpak AD column (Method H) to afford Example 4A (0.124 g, 36%) and Example 4B (0.116 g, 33%).

Example 2A

R$_f$0.40 (50:50 Hex/EtOAc).; mp 192-195° C.; [α]$^{25}_D$+33.8° (c 0.20, MeOH).; $^1$H NMR (DMSO-d$_6$) δ 1.20-1.42 (m, 4H), 1.58-1.66 (m, 1H), 1.98-2.08 (m, 1H), 2.49-2.73 (m, 1H), 3.30-3.38 (m, 1H), 4.39-4.49 (m, 2H), 4.88-4.92 (m, 2H), 6.42 (d, J=2.8 Hz, 1H), 6.67 (d, J=2.8 Hz, 1H), 6.75 (d, J=8.5 Hz, 2H), 7.23 (d, J=8.5 Hz, 2H), 8.75 (s, 1H), 9.32 (s, 1H).; FAB MS m/z 312 [C$_{19}$H$_{20}$O$_4$]$^+$.; HPLC (Method A) 95.0% (area percent), t$_R$=16.82 min.; % ee (Method G)>99%, t$_R$=4.83 min.; Anal. Calcd for C$_{19}$H$_{20}$O$_4$·0.3H$_2$O: C, 71.82; H. 6.53 Found: C, 71.54, 6.38.

Example 2B

R$_f$0.40 (50:50 Hex/EtOAc).; mp 195-197° C.; [α]$^{25}_D$-31.2° (c 0.27, MeOH). $^1$H NMR (DMSO-d$_6$) δ 1.20-1.42 (m, 4H), 1.58-1.66 (m, 1H), 1.98-2.08 (m, 1H), 2.40-2.73 (m, 1H), 3.30-3.38 (m, 1H), 4.39-4.49 (m, 2H), 4.88-4.92 (m, 2H), 6.42 (d, J=2.8 Hz, 1H), 6.67 (d, J=2.8 Hz, 1H), 6.75 (d, J=8.5 Hz, 2H), 7.23 (d, J=8.6 Hz, 2H), 8.75 (s, 1H), 9.32 (s, 1H).; FAB MS m/z 312 [C$_{19}$H$_{20}$O$_4$]$^+$.; HPLC (Method A)>99% (area percent), t$_R$=16.81 min.; % ee (Method G)>99%, t$_R$=6.83 min.; Anal. Calcd for C$_{19}$H$_{20}$O$_4$·0.1H$_2$O: C, 72.64; H, 6.48. Found: C, 72.72; 6.28.

Examples 3A and 3B

Preparation of (3aR, 4S, 9bS)-6-Ethoxymethyl-4-(4-hydroxy-phenyl)-1,2,3,3a,4,9b-hexahydro-cyclopenta[c]chromen-8-ol (3aS, 4R, 9bR)-6-Ethoxymethyl-4-(4-hydroxy-phenyl)-1,2,3,3a,4,9b-hexahydro-cyclopenta[c]chromen-8-ol

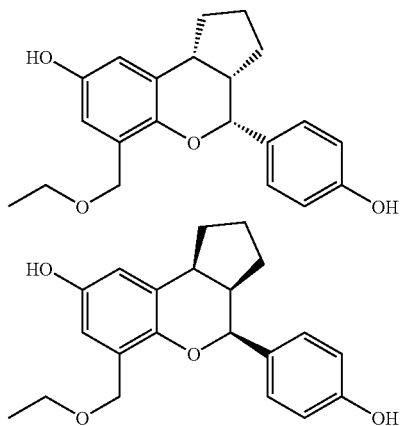

A. Preparation of (±)-[2-(3-Hydroxymethyl-2,5-bis-methoxymethoxy-phenyl)-cyclopentyl]-4-methoxymethoxy-phenyl)-methanone

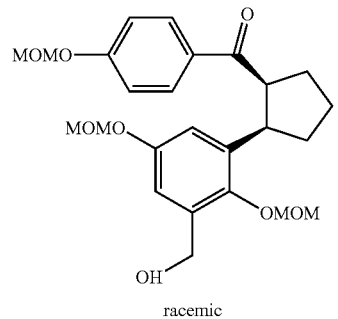

racemic

Prepare a solution of (±)-{2-[3-(tert-butyl-dimethyl-silanyloxymethyl)-2,5-bis-methoxymethoxy-phenyl]-cyclopentyl}-(4-methoxymethoxy-phenyl)-methanone (2.10 g, 3.66 mmo) in THF (100 mL) and cool in an ice-H$_2$O bath to 0° C. Add tetrabutylammonium fluoride TBAF (5.49 mL of a 1 M solution in THF, 5.49 mmol). Remove the ice-H$_2$O bath warm the reaction to ambient temperature over 2 hours. Pour *the solution into H$_2$O (100 mL) and extract with EtOAc (3×50 mL). Combine the organic extracts and wash with brine, dry (MgSO$_4$), filter and concentrate to obtain the subtitled product (1.85 g, >95%) as an oil that may be used without purification. $^1$H NMR (CDCl$_3$) δ 1.72-1.81 (m, 1H), 1.93-2.17 (m 3H), 2.28-2.34 (m, 1H), 2.68-2.73 (m, 1H), 3.40 (s, 3H), 3.45 (s, 3H), 3.61 (s, 3H), 3;66-3.73 (m, 1H), 4.18-4.24 (m, 1H), 4.25-4.45 (m, 2H), 4.83 (d, J=5.9 Hz, 1H), 4.92-5.04 (m, 4H), 5.14 (d, J=5.7 Hz, 2H), 6.64-6.66 (m, 2H), 6.81 (d, J=8.9 Hz, 2H), 7.57 (d, J 8.9 Hz, 2H).

B. Preparation of (±)-5-Bis-methoxymethoxy-3-[2-(4-methoxymethoxy-benzoyl)-cyclopentyl]-benzaldehyde

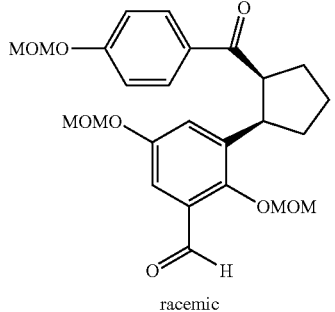

racemic

Add sodium hypochlorite (150 mL) to a solution of (±)-[2-(3-hydroxymethyl-2,5-bis-methoxymethoxy-phenyl)-cyclopentyl]-(4-methoxymethoxy-phenyl)-methanone (1.69 g, 3.66 mmol) and tetrabutylammonium bromide (0.500 g, 1.55 mmol) in EtOAc. Stir the biphasic mixture vigorously for 2 hours at ambient temperature and separate the layers. Extract the aqueous solution with EtOAc (50 mL) and wash the combined organics with H$_2$O (50 mL) and brine (25 mL), then dry (MgSO$_4$), filter and concentrate to obtain the subtitled product (1.88 g, >95%) as an oil that may be used without purification. $^1$H NMR (CDCl$_3$) δ 1.76-1.81 (m, 1H), 1.97-2.14 (m, 4H), 2.24-2.39 (m, 1H), 3.41 (s, 3H), 3.42 (s, 3H), 3.58 (s, 3H), 3.80-3.86 (m, 1H), 4.28-4.33 (m, 1H), 4.94-5.07 (m, 4H), 5,12 (s, 2H), 6.81 (d, J=8.9 Hz, 2H), 7.00 (d, J=3.1 Hz, 1H), 7.08 (d, J=3.1 Hz, 1H), 7.61 (d, J=8.9 Hz, 2H), 10.00 (s, 1H).

C. Preparation of (3aR, 4S, 9bS)-6-Ethoxymethyl-4-(4-hydroxy-phenyl)-1,2,3,3a,4,9b-hexahydro-cyclopenta[c]chromen-8-ol and (3aS, 4R, 9bR)-6-Ethoxymethyl-4-(4-hydroxy-phenyl)-1,2,3,3a,4.9b-hexahydro-cyclopenta[c]chromen-8-ol Add a solution of (±)-5-bis-methoxymethoxy-3-[2-(4-methoxymethoxy-benzoyl)-cyclopentyl]-benzaldehyde (2.43 g, 5.31 mmol) in EtOH (60 mL) to a parr bottle with PtO$_2$ (0.10 g, 0.44 mmol). Hydrogenate the mixture at 10 psi for 2 hours. Filter the reaction through Celite® and concentrate the filtrate to afford the diethyl acetal intermediate. Use conditions analogous to those described in Example 1A and 1B, except using HCl gas in EtOH versus MeOH, cyclize the crude intermediate to obtain racemic material (0.610 g, 34%). Separate the racemic mixture with a Chiralpak AD column (Method B) to afford the Example 5A (0.212 g, 11%) and Example 5B (0.249 g, 13%).

Example 3A

R$_f$0.42 (70:30 Hex/EtOAc).; mp 65-8° C.; [α]$^{25}_D$+28.9° (c 23, MeOH).; $^1$H NMR (DMSO-d$_6$) δ 1.14 (t, J=6.9 Hz, 3H), 1.24-1.44 (m, 4H), 1.61-1.67 (m, 1H), 2.03-2.08 (m, 1H), 2.56-2.73 (m, 1H), 3.36-3.41 (m, 1H), 3.49 (q, J=6.9 Hz, 2H), 4.43 (s, 2H), 4.93 (d, J=1.7 Hz, 1H), 6.47 (d, J=2.8 Hz, 1H), 6.59 (d, J=2.8 Hz, 1H), 6.76 (d, J=8.6 Hz, 2H), 7.24 (d, J=8.4 Hz, 2H), 8.76 (s, 1H), 9.28 (s, 1H).; FAB MS m/z 340 [C$_{21}$H$_{24}$O$_4$]$^+$.; HPLC (Method A) 97.8% (area percent), t$_R$=18.46 min.; % ee (Method C)>99%, t$_R$=10.47 min.

Example 3B

R$_f$0.42 (70:30 Hex/EtOAc).; mp 62-66° C.; [α]$^{25}_D$-22.4° (c 0.17, MeOH).; $^1$H NMR (DMSO-d$_6$) δ 1.14 (t, J=7.0 Hz, 3H), 1.24-1.44 (m, 4H), 1.63-1.67 (m, 1H), 2.03-2.08 (m, 1H), 2.56-2.61 (m, 1H), 3.37-3.43 (m, 1H), 3.49 (q, J=7.0 Hz, 2H), 4.43 (s, 2H), 4.93 (d, J=1.9 Hz, 1H), 6.47 (d, J=2.8 Hz, 1H), 6.59 (d, J=2.6 Hz, 1H), 6.75 (d, J=8.6 Hz, 2H), 7.24 (d, J=8.4 Hz, 2H), 8.76 (s, 1H), 9.28 (s, 1H).; FAB MS m/z 340 [C$_{21}$H$_{24}$O$_4$]$^+$.; HPLC (Method A) 98.6% (area percent), t$_R$=18.48 min.; % ee (Method C)>99%, t$_R$=15.91 min.

Test Procedures

ER Binding Assay

The competition ER binding assay was run in a buffer containing 50 mM N-[2-hydroxyethyl]piperazine-N'-[2-ethanesulfonic acid (Hepes) pH 7.5, 1.5 mM EDTA, 150 mM NaCl, 10% glycerol, 1 mg/mL ovalbumin, 5mM DTT, 0.025 µCi per well of $^3$H-Estradiol(NEN #NET517 at 118 Ci/mmol, 1 mCi/mL), and 10 ng/well ERAlpha or ERbeta Receptor (PanVera). Competing compounds were added at 10 different concentrations. Non-specific binding was determined in the presence of 1 µM of E2 (17-β Estradiol, Sigma, St. Louis, Mo.). The binding reaction (140 µL) was incubated for 4 hours at room temperature, then 70 µL of cold dextran coated charcoal (DCC) buffer was added to each reaction (DCC buffer was prepared by adding 0.75 g of charcoal [Sigma] and 0.25 g of dextran [Pharmacia] per 50 mL of assay buffer). The incubation plates were mixed for 8 minutes on an orbital shaker at 4° C. and then centrifuged at 3,000 rpm for 10 minutes at 4° C. An aliquot of 120 µl of the mix was transferred to another 96-well, white flat bottom plate (Costar) and 175 µl of Wallac Optiphase Hisafe 3 scintillation fluid was added to each well. The plates were sealed and then shaken vigorously on an orbital shaker. After an incubation of 2.5 hrs, the radioactivity was counted in a Wallac Microbeta counter. The IC$_{50}$ and percent inhibition at 10 µM were calculated. The K$_d$ for $^3$H-Estradiol was determined by saturation binding to ERα and ERβ receptors. The IC$_{50}$ values for compounds were converted to K$_i$ values using the Cheng-Prusoff equation and the K$_d$ values were determined by saturation binding assay. Compounds of Examples 1-5 are active in the assay as described. Preferred compounds bind to the ER beta receptor with a K$_i$ of less than 20 nM. More preferred compounds bind to the ER beta receptor with a K$_i$ of less than 1 nM. Compounds that are selective to binding to the ER beta receptor compared to the ER alpha receptor bind to the ER beta receptor with a lower K$_i$ compared to the K$_i$ for the ER alpha receptor.

As determined by the above assay, the compounds of Examples 1-3 exhibit binding affinitites (Kis) at the ER Alpha subtype in the range 11.9→10,000 nM and to the ER Beta subtype in the range of 0.28-184 nM.

LNCaP Human PCa Xenograft Assay

ERbeta agonists are evaluated for their effects on the growth of androgen-sensitive LNCaP human prostatic cancer (PCa) xenografts grown in intact sexually mature (5-6 weeks old) Hsd: Athymic Nude-nu (Athymic Nude) male mice. 2.0×10$^6$ LNCaP tumor cells are injected bilaterally by the subcutaneous route into the pre-tracheal region of testicular intact male mice. Mice are castrated via the scrotal route to serve as the positive control group. Test compounds are administered once per day by subcutaneous or gavage administration at multiple dose levels in a volume of 0.2 ml to xenograft-bearing mice starting on the day following tumor injection. Test compounds are reformulated weekly based on average group mean body weights. The vehicle for these studies is 1% carboxymethyl cellulose (CMC) with 0.25% Tween 80. Body weights and tumor measurements are recorded on a weekly basis and entered directly into a JMP™ (SAS; Cary, N.C.) spreadsheet from electronic caliper measurement. Tumor volumes in $mm^3$ are calculated in JMP using the following formula: L×W×H×0.5236. Tumor and body weight responses for individual mice are recorded on a weekly basis. When LNCaP tumor volumes enter log-phase expansion, lesions are measured every 3-4 days. Growth rates are determined using linear modeling of the log tumor values and time to treatment failure (tumor vol=1300-1500 $mm^3$) are determined using a linear extrapolation model (SAS; Cary, N.C.). Because of humane animal use considerations, animals are sacrificed when their tumor volumes approach 1200-1400 $mm^3$. At necropsy, final tumor measurement and body weights are recorded and whole blood is obtained via cardiac puncture and allowed to clot on ice. Serum is transferred to appropriately labeled 0.5 ml Eppendorf micro tubes, and samples are stored at −80° C. for biomarker analysis.

General Rat Preparation Procedure

Seventy-five day old (unless otherwise indicated) female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room was 12 hours light and 12 hours dark.

Dosing Regimen Tissue Collection: After a one week acclimation period (therefore, two weeks post-OVX) daily dosing with a compound of formula (I) ("F—I") is initiated. 17α-ethynyl estradiol or F—I is given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, v:v) mixture and a blood sample is collected by cardiac puncture. The animals are then sacrificed by asphyxiation with $CO_2$, the uterus is removed through a midline incision, and a wet uterine weight is determined. 17α-ethynyl estradiol is obtained from Sigma Chemical Co., St. Louis, Mo.

Cardiovascular Disease/Hyperlipidemia

The blood samples from above are allowed to clot at room temperature for 2 hours, and serum is obtained following centrifugation for 10 minutes at 3000 rpm. Serum cholesterol is determined, using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

The uteri from above are kept at 4° C. until time of enzymatic analysis. The uteri are then homogenized in 50 volumes of 50 mM Tris buffer (pH 8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosinophils in the uterus is an indication of estrogenic activity of a compound. The maximal velocity of a 15 second interval is determined over the initial, linear portion of the reaction curve.

Inhibition of Bone Loss (Osteoporosis) Test Procedure

Following the general preparation procedure described above, the rats are treated daily for thirty-five days (6 rats per treatment group) and sacrificed by carbon dioxide asphyxiation on the 36th day. The thirty-five day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized X-rays generated and analyzed by an image analysis program (NIH image) at the distal metaphysis. The proximal aspect of the tibiae from, these animals are also scanned by quantitative computed tomography. In accordance with the above procedures, F—I or ethynyl estradiol ($EE_2$) in 20% hydroxypropyl β-cyclodextrin are-orally administered to test animals.

Therapeutic Methods of Use and Dosages

Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (I).

As used herein, the term "patient" refers to a warm blooded animal such as a mammal that is afflicted with a particular estrogen receptor-beta mediated disease. It is understood that guinea pigs, dogs, cats, rats, mice, horses, cattle, sheep, and humans are examples of animals within the scope of the meaning of the term.

As used herein, the term "therapeutically effective amount" of a compound of formula (I) refers to an amount which is effective in controlling diseases and conditions associated with estrogen receptor-beta mediated diseases such-as prostate cancer, benign prostatic hyperplasia, testicular cancer, cardiovascular diseases, neurodegenerative disorders, urinary incontinence, CNS disorders, GI tract disorders, and osteoporosis. The term "controlling" is intended to refer to all processes wherein there may be a slowing, interrupting, arresting, or stopping of the progression of the diseases and conditions described herein, but does not necessarily indicate a total elimination of all disease and condition symptoms, but does include prophylactic treatment of the diseases and conditions associated with estrogen receptor-beta mediated diseases such as prostate cancer, benign prostatic hyperplasia, testicular cancer, cardiovascular diseases, neurodegenerative disorders, urinary incontinence, CNS, GI tract disorders and osteoporosis.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (I) is expected to vary from about 0.001 milligram per kilogram of body weight per day (mg/kg/day) to about 100 mg/kg/day. Preferred amounts can be determined by one skilled in the art.

In effecting treatment of a patient afflicted with the diseases and conditions described above, a compound of formula (I) can be administered in any form or mode which makes the compound bioavailable in a therapeutically effective amount, including oral, inhalation, and parenteral routes. For example, compounds of formula (I) can be administered orally, by inhalation of an aerosol or dry powder, subcutaneously, intramuscularly, intravenously, transdermally, intranasally, rectally, topically, and the like. Oral or inhalation administration is generally preferred for treatment of respiratory diseases, e.g. asthma. One skilled in the art of preparing formulations can readily select the proper form and mode of administration depending upon the particular characteristics of the compound selected, the disease or condition state to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (I) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (I) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system that dispenses the compounds of the present invention or a formulation thereof. Formulations for administration by inhalation of compounds of formula (I) may be delivered in single phase, bi-phasic, or tri-phasic systems. A variety of systems are available for the administration by aerosols of the compounds of formula (I). Dry powder formulations are prepared by either pelletizing or milling the compound of formula (I) to a suitable particle size or by admixing the pelletized or milled compound of formula (I) with a suitable carrier material, such as lactose and the like. Delivery by inhalation includes the necessary container, activators, valves, subcontainers, and the like. Preferred aerosols and dry powder formulations for administration by inhalation are able to be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (I) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

We claim:

1. A compound of the formula:

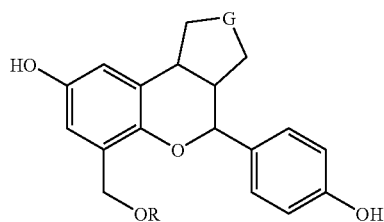

(I)

wherein R is hydrogen or $C_1$-$C_6$alkyl; and
G is —$CH_2$— or —$CH_2CH_2$—;
or a pharmaceutically acceptable salt thereof.

2. A compound selected from the group consisting of:
a) (3aR, 4S, 9bS)-4-(4-Hydroxy-phenyl)-6-methoxymethyl-1,2,3,3a,4,9b-hexahydro-cyclopenta[c]chromen-8-ol;
b) (3aS, 4R, 9bR)-4-(4-Hydroxy-phenyl)-6-methoxymethyl-1,2,3,3a,4,9b-hexahydro-cyclopenta[c]chromen-8-ol;
c) (3aR, 4S, 9bS)-6-Hydroxymethyl-4-(4-hydroxy-phenyl)-1,2,3,3a,4,9b-hexahydro-cyclopenta[c]chromen-8-ol;
d) (3aS, 4R, 9bR)-6-Hydroxymethyl-4-(4-hydroxy-phenyl)-1,2,3,3a,4,9b-hexahydro-cyclopenta[c]chromen-8-ol;
e) (3aR, 4S, 9bS)-6-Ethoxymethyl-4-(4-hydroxy-phenyl)-1,2,3,3a,4,9b-hexahydro-cyclopenta[c]chromen-8-ol; and
f) (3aS, 4R, 9bR)-6-Ethoxymethyl-4-(4-hydroxy-phenyl)-1,2,3,3a,4,9b-hexahydro-cyclopenta[c]chromen-8-ol;
and the pharmaceutically acceptable salts thereof.

3. A compound according to claim 1 of the formula:

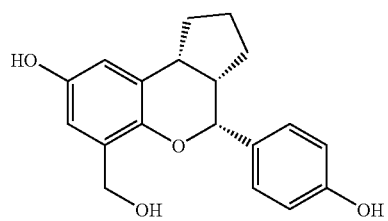

or a pharmaceutically acceptable salt thereof.

4. A compound according to claim 1 of the formula:

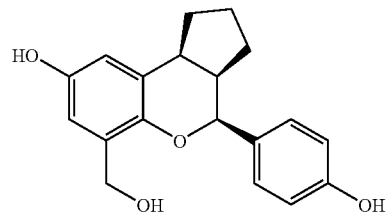

or a pharmaceutically acceptable salt thereof.

5. A compound according to claim 1 of the formula:

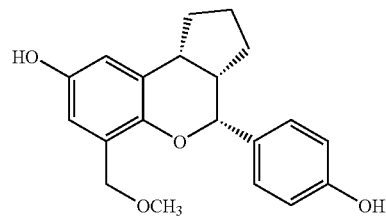

or a pharmaceutically acceptable salt thereof.

6. A compound according to claim 1 of the formula:

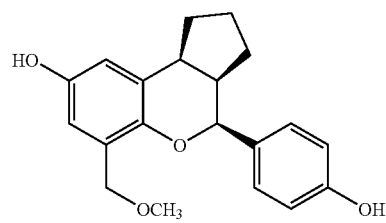

or a pharmaceutically acceptable salt thereof.

7. A compound according to claim 1 of the formula:

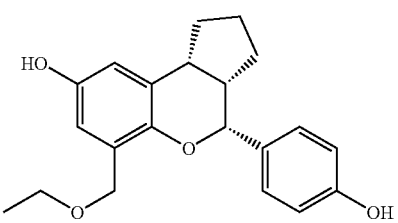

or a pharmaceutically acceptable salt thereof.

8. A compound according to claim 1 of the formula:

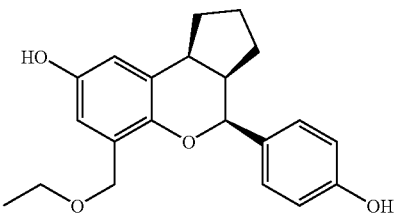

or a pharmaceutically acceptable salt thereof.

9. A pharmaceutical composition comprising a compound of claim 1 and a pharmaceutically acceptable carrier.

10. A method of treating prostate cancer in a patient in need thereof comprising administering to said patient a therapeutically effective amount of a compound of claim 1.

11. A method of treating benign prostatic hyperplasia in a patient in need thereof comprising administering to said patient a therapeutically effective amount of a compound of claim 1.

12. A method according to claim 11 wherein said patient is a human.

* * * * *

UNITED STATES PATENT AND TRADEMARK OFFICE
CERTIFICATE OF CORRECTION

PATENT NO. : 7,279,499 B2  Page 1 of 1
APPLICATION NO. : 10/549106
DATED : October 9, 2007
INVENTOR(S) : Gregory Lee Durst et al.

It is certified that error appears in the above-identified patent and that said Letters Patent is hereby corrected as shown below:

On the Title page:
Insert --(60) Related U.S. Application Data
Provisional application no. 60/464,405 filed April 21, 2003--.

Col. 1 line 4 of the specification, insert the following
cross-reference after the title:
--This application is the national phase application, under
35 USC 371, for PCT/US2004/009271, filed April 8, 2004, which
claims the benefit, under 35 USC 119(e) of US provisional
application 60/464,405 filed April 21, 2003.--

Signed and Sealed this

Twenty-third Day of November, 2010

David J. Kappos
*Director of the United States Patent and Trademark Office*